(12) United States Patent
Deyoung et al.

(10) Patent No.: US 11,519,603 B2
(45) Date of Patent: Dec. 6, 2022

(54) CARBON MONOXIDE DETECTOR AND CONTROL SYSTEM AND METHOD OF OPERATION

(71) Applicant: USSC ACQUISITION CORP., Exton, PA (US)

(72) Inventors: Perry Deyoung, Ada, MI (US); Daniel A. Paulsen, Walker, MI (US)

(73) Assignee: USSC ACQUISITION CORP., Exton, PA (US)

( * ) Notice: Subject to any disclaimer, the term of this patent is extended or adjusted under 35 U.S.C. 154(b) by 961 days.

(21) Appl. No.: 16/261,456

(22) Filed: Jan. 29, 2019

(65) Prior Publication Data

US 2019/0293288 A1   Sep. 26, 2019

Related U.S. Application Data

(60) Provisional application No. 62/623,284, filed on Jan. 29, 2018.

(51) Int. Cl.
| | |
|---|---|
| *F23N 5/24* | (2006.01) |
| *F02N 11/10* | (2006.01) |
| *G01N 27/413* | (2006.01) |
| *G01N 33/00* | (2006.01) |

(52) U.S. Cl.
CPC ............ *F23N 5/245* (2013.01); *F02N 11/10* (2013.01); *G01N 27/413* (2013.01); *G01N 33/004* (2013.01)

(58) Field of Classification Search
CPC .............................. F02N 11/10; G01N 33/004
See application file for complete search history.

(56) References Cited

U.S. PATENT DOCUMENTS

| | | | | |
|---|---|---|---|---|
| 8,725,329 | B1* | 5/2014 | Snyder | B63H 20/14 701/21 |
| 10,819,100 | B1* | 10/2020 | Andrade | G01N 33/0063 |
| 2007/0085692 | A1* | 4/2007 | Grant | G08B 21/14 340/632 |
| 2007/0200719 | A1* | 8/2007 | Adkins | G01N 33/004 340/632 |
| 2009/0251325 | A1* | 10/2009 | Smith | G08B 21/14 340/632 |
| 2010/0171608 | A1* | 7/2010 | Harkins | G08B 21/14 340/506 |
| 2010/0201531 | A1* | 8/2010 | Pakravan | G08B 29/20 340/632 |
| 2011/0062725 | A1* | 3/2011 | Cristoforo | F02D 29/06 290/40 R |
| 2013/0093593 | A1* | 4/2013 | Woods | G08B 17/10 340/628 |

OTHER PUBLICATIONS

FIREBOT-XINTEX, Model:CO Sentinel Marine Carbon Monoxide Alarm CMD-4M, CMD-4MR Jun. 2009.*

* cited by examiner

*Primary Examiner* — Logan M Kraft
*Assistant Examiner* — Arnold Castro
(74) *Attorney, Agent, or Firm* — Faegre Drinker Biddle & Reath LLP

(57) ABSTRACT

A carbon monoxide detector and control system for internal combustion engine or heating devices and a method of operating the carbon monoxide detector system.

17 Claims, 4 Drawing Sheets

CARBON MONOXIDE DETECTOR AND CONTROL SYSTEM AND METHOD OF OPERATION

CROSS-REFERENCE TO RELATED APPLICATIONS

This application claims the benefit of U.S. Provisional Application Patent Ser. No. 62/623,284, filed Jan. 29, 2018, the entire disclosure of which is hereby incorporated herein by reference.

BACKGROUND

1. Field

The present invention relates to a carbon monoxide detector and control system for carbon monoxide producing devices, such as heating devices and internal combustion engines, including portable power equipment, as well as a method of operating the carbon monoxide detector and control system in connection with such devices. More specifically the present invention relates to a carbon monoxide detector and control system for shutting off or preventing the starting of an internal combustion engine, or a heating device when carbon monoxide levels exceed a set limit or are increasing. The present invention is particularly applicable and useful in combination with devices or equipment that may be moved between interior and exterior spaces or equipment or devices designed to be movable, such as portable power equipment or heating devices, including generators for RVs and travel trailers, even if they are securely fixed in place.

2. Description of the Prior Art

Portable power equipment advantageously enables users to save time and provide various conveniences in daily life, including providing electrical power when power from the electrical grid is not readily available. Depending on the particular application, such portable power equipment is commonly powered by internal combustion engines that burn fuel, such as propane, kerosene, gasoline, or diesel fuel. Portable generators are also commonly used to provide electricity in remote locations or when conventional electrical systems are not available (i.e., during a power outage, off-grid locations, or for movable equipment such as trailers, movable offices, RVs, boats and more). Aside from their convenience, portable power equipment such as portable generators have the potential to harm users of the devices due to their ability to produce carbon monoxide (CO) gas. Heaters that burn a fuel, such as propane or kerosene or other fuels, have the same issue as internal combustion engines. The potential for harm may occur for a variety of reasons. For example, the primary cause of harm to individuals is from using carbon monoxide producing devices in enclosed spaces, but harm may occur due to improper or misuse by the operator, poor maintenance, improper application, or even poor design. More specifically, under certain environmental conditions, particularly during inclement weather, or out of convenience, users commonly use such portable power equipment or heating devices in enclosed spaces, such as in a garage, basement, construction site, or enclosed spaces in remote areas, which may cause a harmful buildup of carbon monoxide. This improper use occurs even though the manufacturers of such devices provide ample warning on the machines and in the operator's manual.

Carbon monoxide is a colorless, odorless, tasteless gas that is produced by the incomplete combustion of fuels including wood, natural gas, gasoline, diesel, kerosene, coal, charcoal, and other fuels. As it is colorless, odorless, and tasteless, it is near impossible to identify by individuals except from the effects on the individual, but such effects make it hard for individuals to respond. Carbon monoxide is caused by lack of oxygen or a disruption in the burning process of the fuel. Carbon monoxide is especially dangerous if it is allowed to build up in enclosed or semi-enclosed spaces and may potentially poison and eventually kill people and animals. As an internal combustion engine uses up oxygen (which it requires to operate) in an enclosed space, and as the levels of carbon monoxide that are generated by an internal combustion engine increase, it causes an exponential production and buildup of carbon monoxide in the enclosed space. Even well maintained engines produce some carbon monoxide, and the more carbon monoxide that is sucked into the combustion chamber of the engine, the more the combustion process is disrupted, causing more carbon monoxide, thereby creating the mentioned exponential build-up. Depending on the size of the enclosed space and the number and size of devices producing carbon monoxide, as well as any of the above factors, such as maintenance, design, and other factors, the carbon monoxide levels may quickly go from safe for humans to unsafe, and as discussed below, people quickly are incapacitated, and unable to respond to the situation.

Carbon monoxide generally bonds to hemoglobin stronger than carbon dioxide and oxygen, and as such blocks the availability of oxygen which living cells need to function. It does so because of its attraction to hemoglobin in the bloodstream and can cause symptoms such as headaches, fatigue, nausea, and most problematic, confusion. If levels of carbon monoxide rise to certain levels, it can even cause loss of consciousness, and eventually brain damage or death. Although manufacturers are continually trying to reduce the CO output of internal combustion engines, some existing internal combustion engines may have exhaust plumes that exceed 60,000 ppm of carbon monoxide (CO), especially under certain conditions, such as described above. Not only is the buildup of CO problematic, but the engine will also use up available oxygen if operated in an enclosed space. Therefore, even though manufacturers diligently warn consumers against using such portable power equipment in an enclosed room or garage, many people ignore such warnings, even though dangerous levels of CO can quickly occur. Many people have a hard time comprehending the danger that something they cannot sense through sight, touch, taste, or smell could kill them.

Like portable power equipment employing internal combustion engines, other devices such as heating devices, whether large units permanently affixed or portable dryers, stoves, and more, can also generate carbon monoxide gas. Most problematic are portable or smaller heating devices are commonly used for various tasks, such as providing warmth on a cold day, particularly if used in an enclosed space, or even cooking foods, as the burning of the fuel may generate carbon monoxide in a similar fashion as described above with regards to internal combustion engines. A kerosene heater, for example, burns kerosene to provide warmth, but if used in an enclosed space without proper venting, a lack of oxygen or incomplete burning process can lead to the generation of carbon monoxide, which may exponentially increase. Of course, built in furnaces, boilers, and other heating devices may also be problematic, such as when a unit operates with a cracked heat exchanger.

While carbon monoxide alarms are available for use in businesses and homes, such alarms are generally directed to or limited to alerting individuals of the presence of carbon monoxide (similar to the function of a smoke detector for alerting those around of the presence of smoke) without taking any corrective or preventative action. As such, an alarm may activate notifying a user of an issue, but depending on the time from activation of the alarm and an investigation by a user, the carbon monoxide levels may continue to increase, such that a user upon entering the room with elevated carbon monoxide levels may almost immediately experience substantially harmful effects of carbon monoxide poisoning, including even death. In addition, even those exposed to carbon monoxide at lower levels which do not cause a quick death may lose consciousness or be so disoriented that they do not respond properly to any such alerts. While many deaths could be prevented by such alarms, most enclosed rooms, particularly garages and sheds, do not include carbon monoxide alarms, and therefore, there is no way to know if the odorless, colorless carbon monoxide gas is reaching specified levels that are harmful to humans and animals. Even if a building includes a carbon monoxide alarm, it may not be located proximate to the source of carbon monoxide, and as such never alarm, or alarm when it is too late. Thus, there remains a need for improved detection and control of devices that are capable of generating carbon monoxide.

SUMMARY

This section provides a general summary of the present disclosure and is not a comprehensive disclosure of its full scope or all of its features and advantages.

It is an object of the present disclosure to provide a carbon monoxide detector and control system for internal combustion engine and heating devices, and automatically shut down or prevent operation of such engines or devices under specified criteria.

The system includes a controller and at least one sensor in communication with the controller for detecting carbon monoxide gas levels. The system also includes a control actuator subassembly electrically coupled to the controller. The controller is configured to determine if the detector is located indoors or outdoors. If a determination is made that the detector is located inside, shutoff of the internal combustion engine will occur if the detector determines that carbon monoxide levels exceed a preset threshold. If the detector determines that it is located outdoors, it will not initiate a shutdown if the sensor determines the preset maximum level is exceeded; however, the detector may also be configured also to initiate a shutdown if it detects an average of increasing levels of carbon monoxide, and the average exceeds a preset level. In addition, the preset levels may be set differently for the indoors and outdoors configuration.

According to another aspect of the disclosure, a method of operating a carbon monoxide detector and control system is also provided. One advantage of the current invention is that it is always on always measuring levels of CO, so it can prevent the engine or device from starting, preventing override of the device.

The system may include a control system for a device having an on state and an off state and wherein the device is capable of producing carbon monoxide in the on state. The control system includes a control actuator, configured to switch the device between the on state and the off state, and a carbon monoxide detector in communication with the control actuator. The carbon monoxide detector includes a battery, a sensor configured to determine the levels of carbon monoxide proximate to the device capable of producing carbon monoxide and a controller in communication with the sensor and wherein the controller outputs a control signal to the control actuator upon sensing at least one a first condition or a second condition, and wherein the first condition is a carbon monoxide level above a predetermined maximum threshold, and the second condition is a rising average of carbon monoxide levels, that exceeds a preset level.

The control actuator is typically a physical relay having a first position and a second position, corresponding to the on-state and the off-state. The controller monitors whether the physical relay is in the first position or the second position. The controller changes the physical relay from the first position to the second position in response to either of the first or second conditions.

If the physical relay is determined to be in the first position while either of the first or second condition exist, the controller may send a control signal to the physical relay to change from the first position to the second position. The control system may further include a temperature sensor, an indicator LED and an audible alarm. The indicator LED provides an indication of whether the first or second condition exists, and the audible alarm provides indication of at least one of battery low level or end of life of the sensor.

The sensor may be an electrochemical sensor configured to analyze the level of current. More specifically, the controller is configured to compare readings from the electrochemical sensor to a calibration reference to determine level of carbon monoxide.

The device includes at least one of a heater or an internal combustion engine, such as a portable heater or a portable generator.

The present invention also includes a method of controlling a device having an on-state and an off-state and capable of producing carbon monoxide in the on state, the control system including a control actuator, a sensor, and a controller in communication with the control actuator and the sensor. More specifically the method includes the steps of: sensing with the sensor a carbon monoxide level proximate to the device; communicating the carbon monoxide levels from the step of sensing to the controller; determining with the controller the presence of a rising average of carbon monoxide levels; comparing the rising average of carbon monoxide levels to a predetermined rising average threshold level, upon determining that a rising average of carbon monoxide levels exists during the determining step; and activating the control actuator with the controller to ensure that the device is in the off-state in response to the step of comparing showing that the rising average of carbon monoxide levels exceeds the predetermined threshold.

The step of determining may include a step of determining a rising average over a set period of time. The method further includes the step of determining if the device is located in an enclosed space or outside and activating the control actuator with the controller to ensure that the device is in the off-state in response to determining that the device is located in an enclosed space.

The steps of sensing, determining, comparing and activating may occur before a user attempts to initiate the on state with the device. The method may include a step of preventing initiation of the on state with the control actuator in response to the rising level of carbon monoxide exceeding the predetermined threshold level in the step of comparing. The step of determining may include determining with the controller if the level of carbon monoxide sensed in the step of sensing exceeds a predetermined level.

The method may include a step of changing the on state to the off state with the control actuator in response to determining that the level of carbon monoxide exceeds a rising average, in the step of determining. The method may further include a step of preventing initiation of the on state with the control actuator in response to determining that the level of carbon monoxide exceeds a maximum threshold. The method may further include a step of changing the on state to the off state with the control actuator in response to determining that the level of carbon monoxide exceeds a maximum threshold.

The step of sensing may include measuring the current output of the sensor and further including the step of calculating the accumulation levels of carboxyhemoglobin that would be occurring in the human body.

The method may further include a step of performing a self-diagnostic on at least one of the carbon monoxide sensor, control actuator and battery capacity. The method may further include a step of determining the carbon monoxide levels are below a preset low limit while the control actuator is in the off-state in response to the step of activating and further including the step of instructing the control actuator with the controller to be in the on-state. The method may include a step of clearing alarm indicators in response to the step of determining the carbon monoxide levels are below a preset low limit, and may further include a step of multiple cycles of determining the carbon monoxide levels are below a preset low limit before performing the step of instructing the control actuator with the controller to be in the on-state.

The method of controlling a device having an on-state and an off-state and capable of producing carbon monoxide in the on state, the control system including a control actuator, a sensor, and a controller in communication with the control actuator and the sensor, may further include the steps of: sensing with the sensor a carbon monoxide level proximate to the device; communicating the carbon monoxide levels from the step of sensing to the controller; determining with the controller based on communicated carbon monoxide levels if the device is located in an enclosed area or outdoors; and activating the control actuator with the controller to ensure that the device is in the off-state in response to determining that the device is located in an enclosed are during the step of determining. In addition, the method may further include the steps of determining that the carbon monoxide level does not exceed a predetermined threshold; and determining that the carbon monoxide level does not exceed a predetermined rising average. The method further includes the steps of: determining that the carbon monoxide levels are below a preset low threshold; deactivating the control actuator to allow the control actuator to enter a run state in response to determining that the carbon monoxide levels are below a preset low threshold; and clearing any alarm conditions. The method may repeat the steps in a cycle at regular intervals.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

In the following description, details are set forth to provide an understanding of the present disclosure. In some instances, certain circuits, structures and techniques have not been described or shown in detail in order not to obscure the disclosure.

In general, the present disclosure relates to a carbon monoxide detector and control system of the type well-suited for use in various internal combustion engine and heating device applications. The carbon monoxide detector and control system and associated methods of operation of this disclosure will be described in conjunction with one or more example embodiments. However, the specific example embodiments disclosed are merely provided to describe the inventive concepts, features, advantages, and objectives with sufficient clarity to permit those skilled in this art to understand and practice the disclosure. Specifically, the example embodiments are provided so that this disclosure will be thorough, and will fully convey the scope to those who are skilled in the art. Numerous specific details are set forth, such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail.

Referring to the Figures, wherein like numerals indicate corresponding parts throughout the several views, a carbon monoxide detector and control system 20 for internal combustion engine 10 or heating devices 12 is provided. The internal combustion engine 10 or heating devices 12 intended to be used with the system include, but are not limited to the mentioned examples of a portable generator, a portable heater, a cooking device, and a pump.

Figure 1:
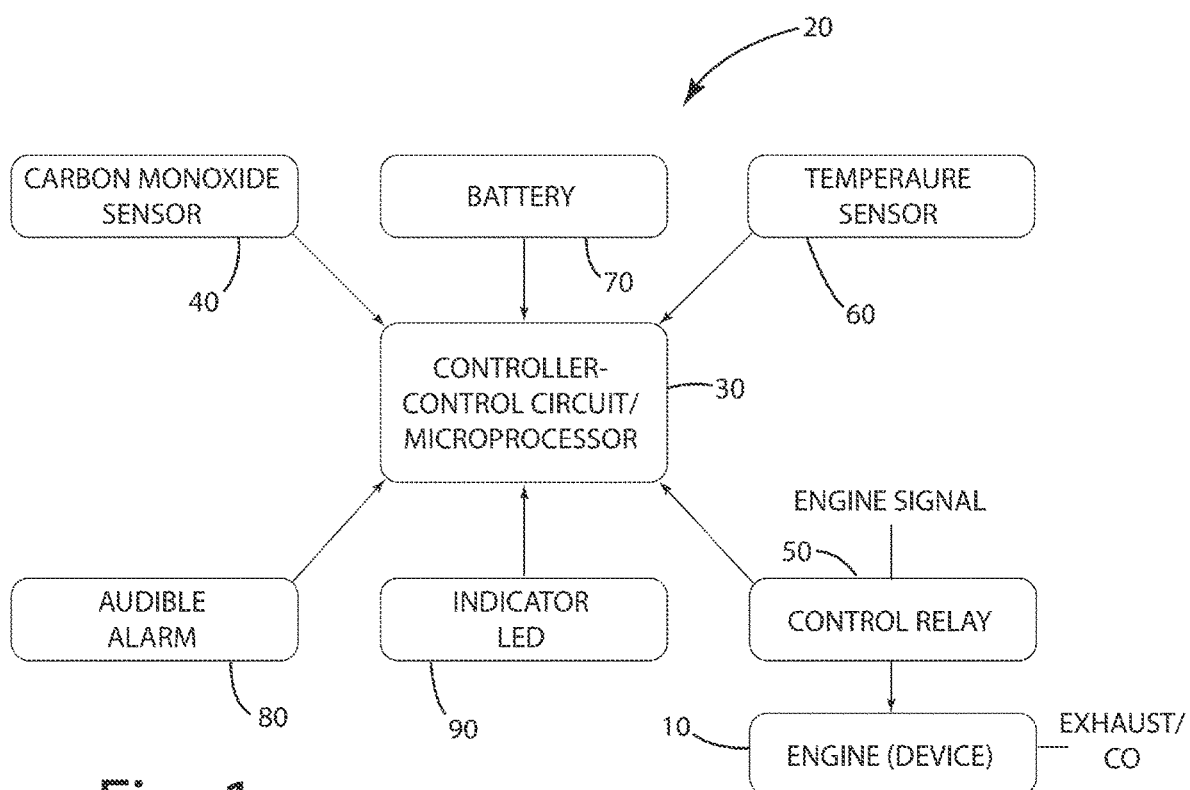
FIG. 1 is a block diagram of the control system used in connection with an internal combustion engine device.
Figure 2:
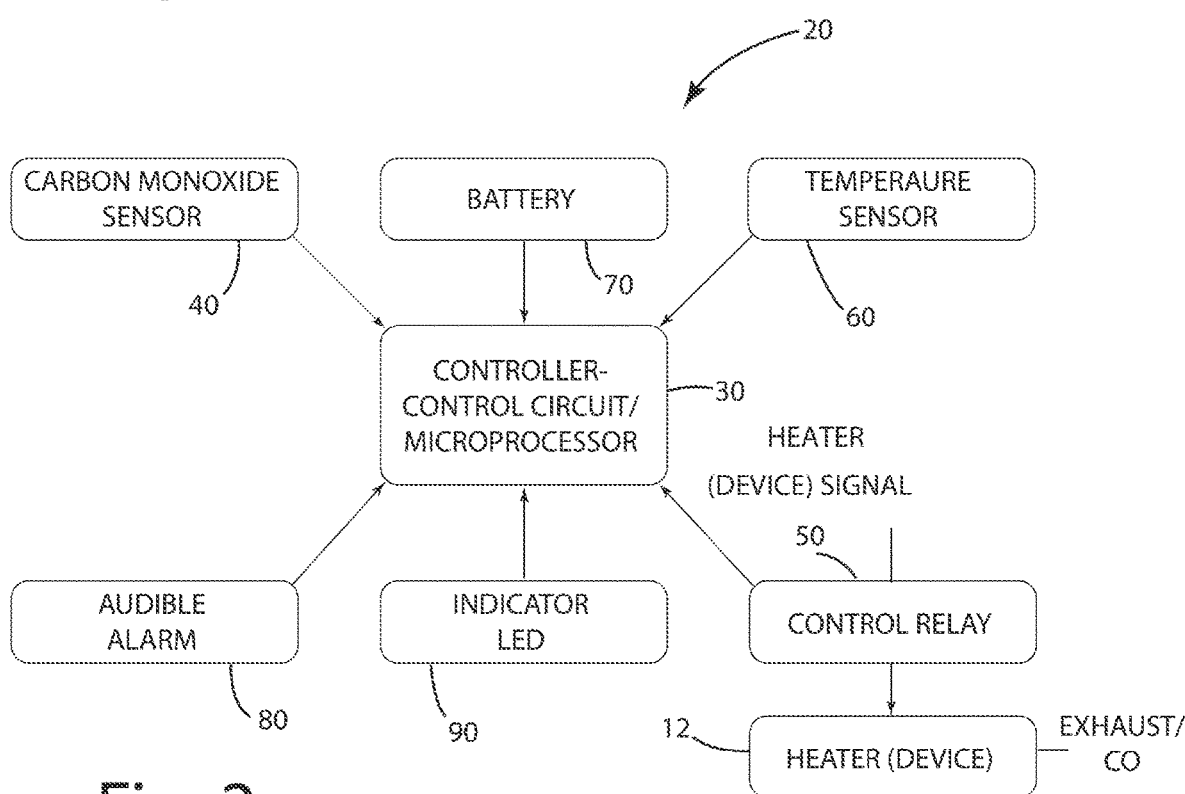
FIG. 2 is a block diagram of the control system used in connection with a heating device.

As best shown in FIGS. 1 and 2, the control system 20 includes a controller 30 and a carbon monoxide sensor 40 in a housing. The controller 30 is disposed in the housing and a display (not shown) may be electrically coupled to the controller 30. It should be appreciated that the controller may not include a display and it is not necessary. The carbon monoxide sensor 40 is capable of determining levels of carbon monoxide and is in communication with the controller (e.g., wired or wirelessly). While the sensor can be coupled directly to the housing, or proximate to the controller 30, the sensor can alternatively be located remotely, such as to protect the sensor 40 from impact, interference, touching, or tampering, and at a position relative to or on the device to receive good readings of carbon monoxide. As such, placement may vary depending on the type of device as well as the size, shape, or configuration of the device. For example, typically it would not be desirable to place the sensor in the direct path of existing exhaust gases as it would typically provide higher than normal readings of carbon monoxide and may cause a temperature differential relative to the ambient environment, which also could lead to inaccurate readings. In addition, it is usually desirable to provide a housing with air flow, such as a cage, which may prevent an object from creating electrical conductivity from the edge to the edge of the sensor, which could cause a faulty reading. In addition, the whole system 20 is configured to be weather resistant and water resistant. As disclosed herein, the sensor 40 is an electrochemical type carbon monoxide sensor; however, it should be understood that other types of sensors may be utilized. A control actuator 50 subassembly in communication with the controller 30 is coupled to the internal combustion engine or heating device in order to shut down the device if the control system detects sufficient levels of carbon monoxide.

The controller 30 is configured to detect faults in the control system and to notify a user of such faults. The controller 30 may provide indication through the indicator LED 90 or the audible alarm 80. The controller 30 is also configured to provide an end-of-life notification and manual self-check. The end-of-life notification is generally the audible alarm, which can provide notification of end of life for the sensor 40 or the battery 70. In the present invention, the system 20 is configured to have a sealed at least 10 year battery, which will typically last longer than the sensor, so the end-of-life notification typically will be the sensor failure signal. However, the detector could as easily be formed with a replaceable battery. Even with current technology, the detector has a ten year life expectancy of the battery 70 and sensor 40. The detector may have an expected life that is less than the portable power equipment or heating device to which it is attached, so it is configured to be easily replaceable. Just the detector portion, which includes the controller 30, battery 70, carbon monoxide sensor 40, temperature sensor 60, audible alarm 80, and indicator LED 90, may be replaced, in some instances as a single unit without the control actuator 50. However in other embodiments the replacement may also include the physical relay; however it is more likely the system 20 will be designed for the control actuator 50 to remain with the device 10, and only the detector portion to be replaced as needed. It is expected that the replacement of the detector will be treated as a maintenance item and built into the maintenance schedule for the device, with the end-of-life indicator acting as a backup to address early battery 70 or sensor 40 failures, or to address the failure to maintain the device 10 in accordance with the scheduled maintenance. The detector's end of life notification may also notify a failure of the temperature sensor or other failures that would prevent accurate readings of carbon monoxide levels. In fact, if there are multiple instances of resetting of the control actuator, specifically the physical relay 50 when the system 20 notices that the relay has been set to a run or on position from the desired off position, it may also trigger the end of life indicators, including the indicator LEDs 90 and audible alarm 80. It is preferable the control actuator 50 or physical relay be biased to an off or stopped state so that the device does not run or start if there is a failure with the carbon monoxide detection system 20.

In more detail, the controller 30 is configured to require a predetermined set point to "trip" the control system (e.g., 50 ppm CO). The trip point, as discussed in greater detail below, may vary depending on the type of device 10, location of the sensor 40 on the device 10, as well as the size, shape, and configuration of the device 10. Many times the carbon monoxide level may be set high while the device 10 is running, as the sensor 40 may be proximate to the exhaust gases, which have a higher concentration of carbon monoxide than after dispersal into the ambient air. The control system 20 may even use two, three, or four set points. For example, a lower rising average and maximum threshold may be used when the device 10 is off, which would prevent starting or initiating use of the device 10, as the readings at the sensor would be more reflective of readings of carbon monoxide in the ambient air, and a higher rising average and/or maximum threshold when the device 10 is already running or operational. For example, different set points may be desirable due to the sensor 40 being mounted on the unit or device 10 close to the ground, not up in the room in which the device is operating. More specifically, the sensor 40, if it is an electrochemical sensor (although other types of sensors may be used), analyzes the electro conductivity. When carbon monoxide is present, an electrolyte, such as water, conducts better and the level of conduction is then compared to either known ppm of carbon monoxide or levels of Carboxyhemoglobin ("COHb") accumulation for the sensed conductivity. Electroconductive or electrolytic detectors are typically the most accurate and sensitive detectors.

In the present invention, the control system may be configured to shut off when the sensor 40 determines that a 10% COHb equivalence exists when the controller 30 determines the device is being used indoors, and at rising levels of COHb equivalence, such as when the rising average exceeds 10% COHb equivalence, when the detector determines the device is being used outdoors. Of course, other COHb equivalence levels may be set to other levels. In addition, if erratic readings are found with no rising average, a higher COHb equivalence level may be set to initiate shutdown.

While the amount of carbon monoxide levels allowed may vary, due to design configurations and placement of the sensor 40 relative to the device 10, particularly the exhaust outlet, generally the maximum preset level of allowed carbon monoxide before shutoff is 250 to 550 ppm, and a rising level of 150 to 280 ppm/minute. In addition, the system 20 may be configured to determine if the device is located outside or in an enclosed space, and initiate shutdown at a much lower level if a determination of enclosed space is determined. Of course, some very large enclosed spaces, like warehouses, have such a large volume of air in the enclosed space, the system 20 would have trouble determining that it is an enclosed space, but at the same time, the ppm of the carbon monoxide would stay low due to the large volume of ambient air surrounding the device, and the system 20 will still be configured to initiate shutdown in response to a rising average or a preset maximum level, as detailed above.

The system 20 may include a temperature sensor 60. As the electroconductivity sensed by the sensor 40 may change with temperature, the controller 30 may use output temperature readings from the temperature sensor to adjust the readings from the carbon monoxide sensor 40. As the present invention is well suited for portable devices, such a portable generators with engines 12, or heaters 14, these may be moved between indoors and outdoors and experience under ranging temperature swings. Adjusting for temperature relative to the sensor 40 readings prevents shutoffs of the device when not needed, as well as failure to shut off when certain levels are reached. The control may be preconfigured to adjust for temperature with the readings from the carbon monoxide sensor 40. More specifically, the carbon monoxide sensor 40 is in the illustrated embodiment an electrochemical sensor, and it measures electro conductivity, so that the conductivity changes by temperature in a known fashion, which the controller may adjust for. Of course the device 10 may heat the area proximate to the sensor 40, so the temperature sensor 60 is typically configured to be proximate to the carbon monoxide sensor 40 to ensure accurate readings.

Figure 4:
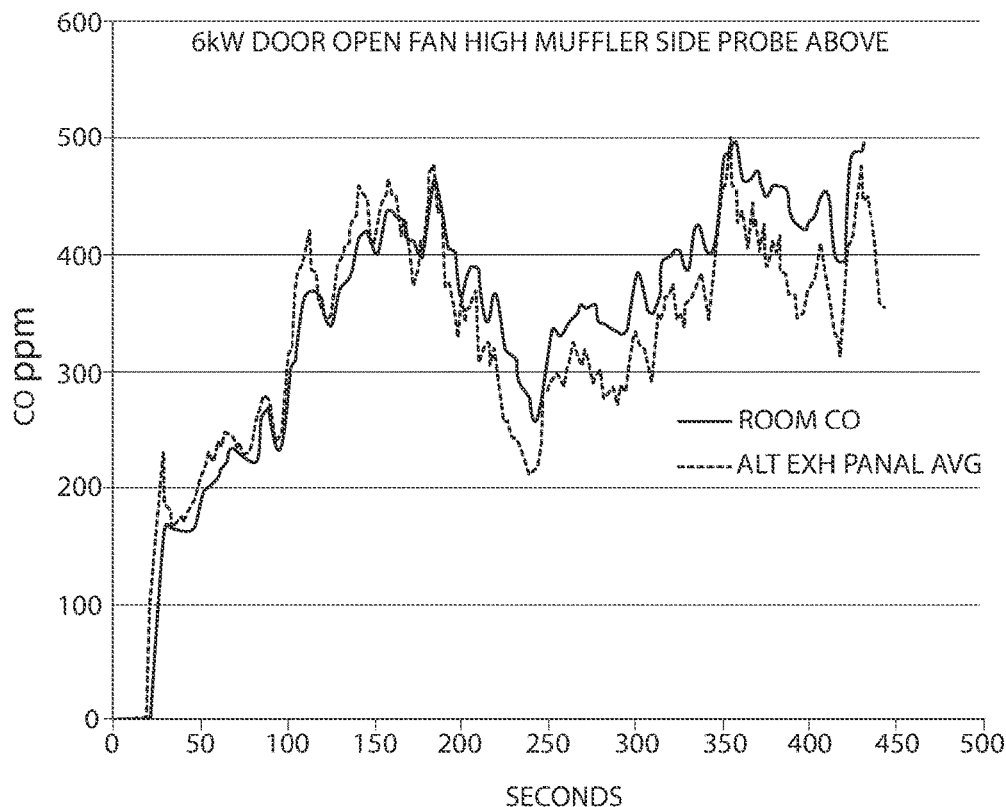
FIG. 4 illustrates a graph of a carbon monoxide level over time in the room and proximate to an internal combustion engine.

According to another aspect, the unit may be powered by a battery (FIG. 4) capable of powering the device for ten years. Alternatively or in addition to the battery, 100 or 245 VAC 60 Hz power may also be available from a magneto coupled to the engine, or even power from an alternator or battery, or other power source on the device 10; however, in such an instance a transformer and filtering would likely be required. Even if the device is battery powered, it still could be tied to the operation of the portable power equipment or heater device, such that the device would be in sleep mode until the portable power equipment or heater device is turned on and then starts measuring CO levels. However, in the preferred embodiment, the system 20 is always measuring the carbon monoxide levels, and will prevent the device from starting or turning on when the levels exceed the preset thresholds, either by maximum thresholds or maximum rising averages. For example, an operator could have multiple devices in an enclosed space, such as a heater and a generator in a garage, and the heater has been running for some time outputting carbon monoxide and other combustion gases into the garage, so when the operator goes to start the generator, it is preferable to prevent starting of the generator, as the generator would add to the carbon monoxide levels and it isn't desirable to wait for the system 20 upon startup of the generator to start measuring, which may take time, particularly time for the system 20 to calculate the rising average, during which the generator is outputting carbon monoxide (in view of the carbon monoxide form the heater and other combustion gases and reduced oxygen in the environment from the heater causing incomplete combustion process in the generator, no matter how well tuned, maintained or how little carbon monoxide is produced by the generator under normal operating conditions).

Figure 5:
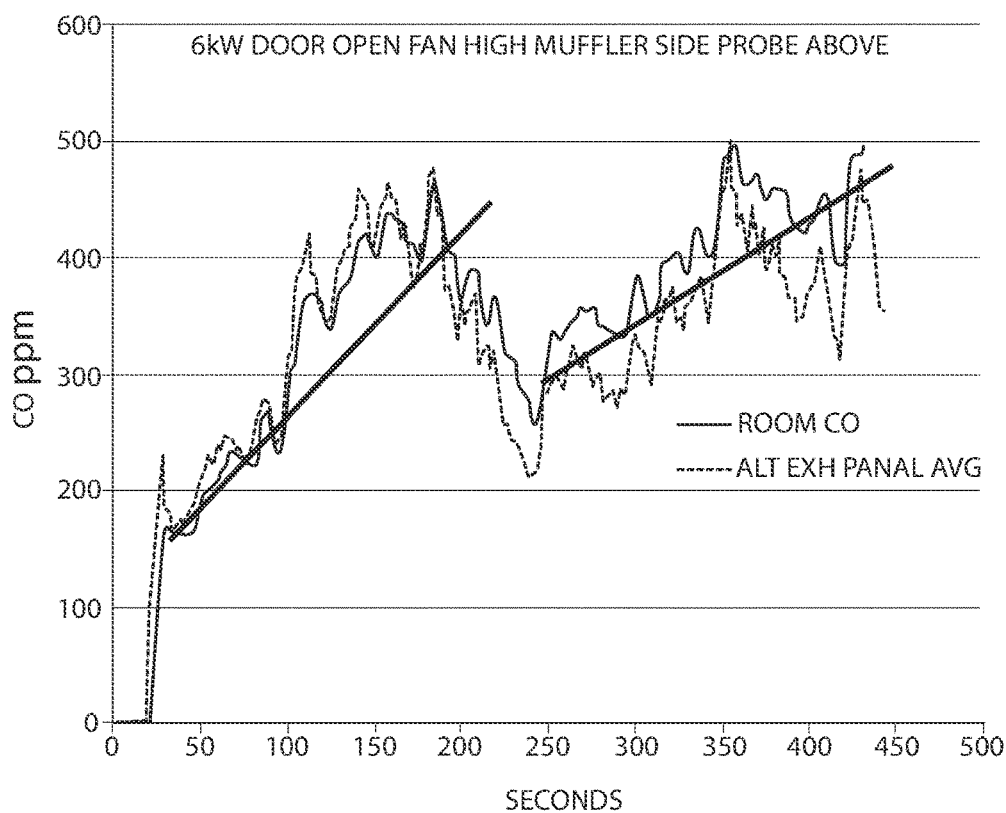
FIG. 5 illustrates the moving average determined by the controller for the carbon monoxide levels in FIG. 4
Figure 6:
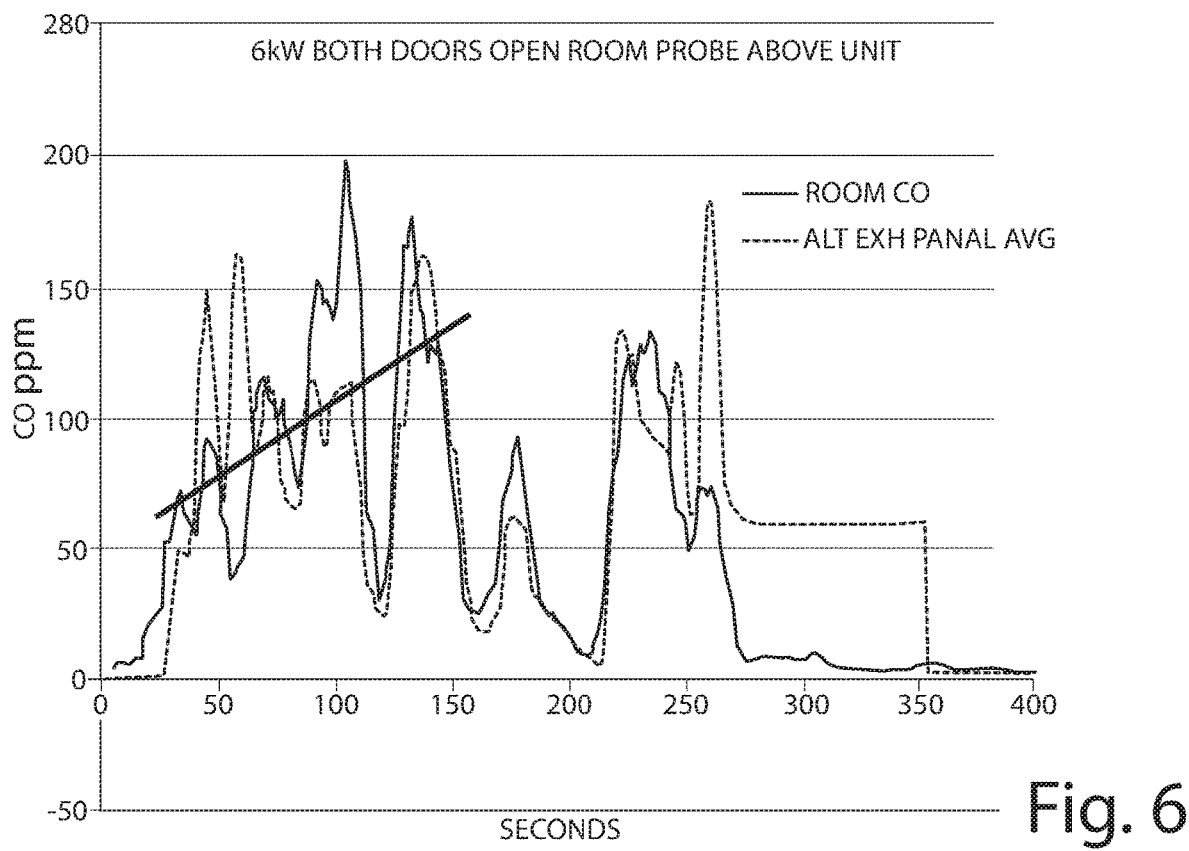
FIG. 6 illustrates a graph of a carbon monoxide level over time in an enclosed space with two open doors, including shut-off effect on levels of carbon monoxide.
Figure 7:
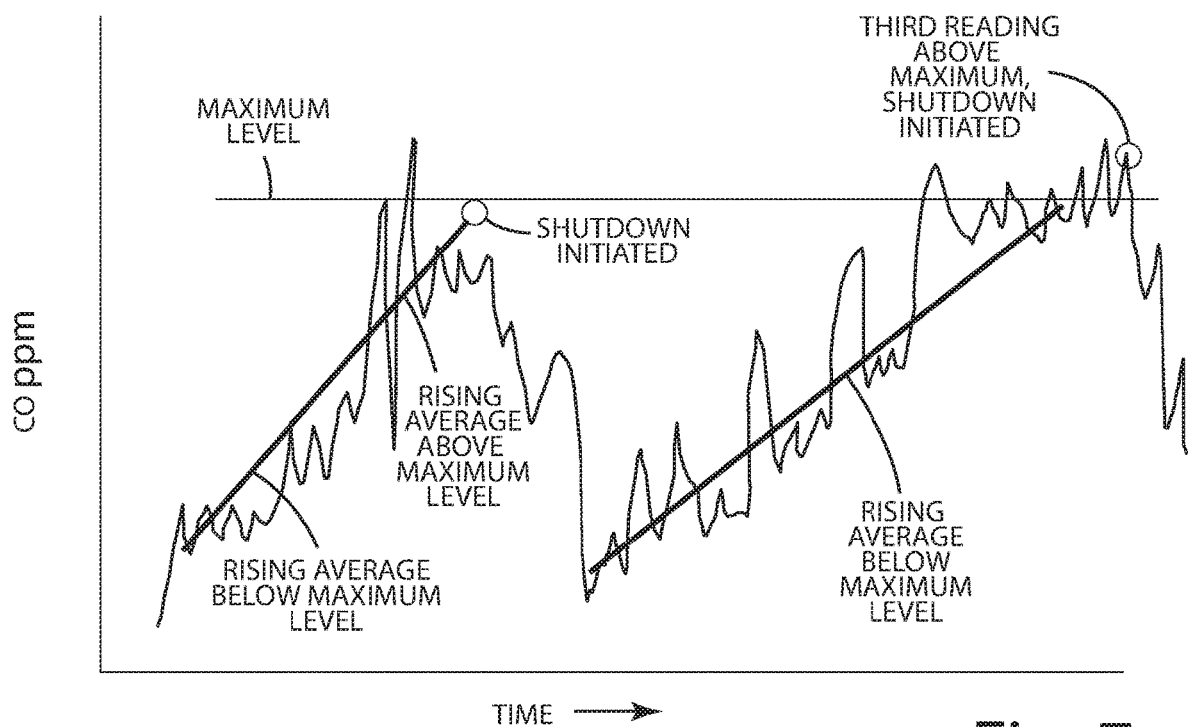
FIG. 7 illustrates a graph of a shutdown protocol for outside operation.

In addition, the carbon monoxide detector system 20, specifically the controller 30 and carbon monoxide sensor 40, is capable of detecting whether device 20, such as the internal combustion engine or heating device, is being utilized in the outdoors or whether it is indoors (i.e., a confined area). Erratic readings from the sensor 40 can be indicative of moving air around the sensor 40 (e.g., wind). However, erratic readings alone cannot conclusively provide confirmation that the system 20 and device 10 are being used outdoors. For instance, a user could be using the system 20 and device 10 in an enclosed space (e.g., indoors) and be operating a fan, such as a fan attached to a heater in the enclosed space, or an HVAC system may have a vent blowing across the device, and more specifically the sensor 40. In such a situation, however, while the readings may be erratic, an average of the readings over time, such as the rising average, could be used to indicate that the device is being operated in an enclosed space, as the level of carbon monoxide would continue to rise even if air is moving within the enclosed space. Upon reaching a set threshold for the rising average the detector may initiate shutdown. FIGS. 5-7 illustrate an exemplary rising average.

In operation, the controller 30 of the system 20 is configured to detect erratic readings (such as those due to wind) from the carbon monoxide sensor 40. If the readings are not erratic, the controller 30 may revert back to a predetermined (lower) detection level. However, if erratic readings are detected, the controller 30 will continue to monitor the sensor 40 readings to detect an overall or average rise in the sensor reading. If an average rise in the sensor reading is detected, the control is initiated and the portable power equipment or heating device is shut down. For example, the normal level of rising average may be 150 ppm/minute, but in an erratic situation, it may increase the rising average allowed to 200 ppm/minute, and with the maximum level may have a maximum level of 250 ppm, but up that to 500 ppm in response to erratic readings. The erratic readings may be due to the exhaust blowing across the sensor 40 with the wind and if control, i.e. shut off, was initiated at a lower level, the device would be cycled off frequently when not necessary. The above numbers are only exemplary and may vary device by device. In addition, the controller 30 may include a counter, which counts the times that the maximum is exceeded, and may cycle through the control method for three times before the controller 30 instructs the control actuator 50 to initiate a shutdown of the device 10.

Figure 3:
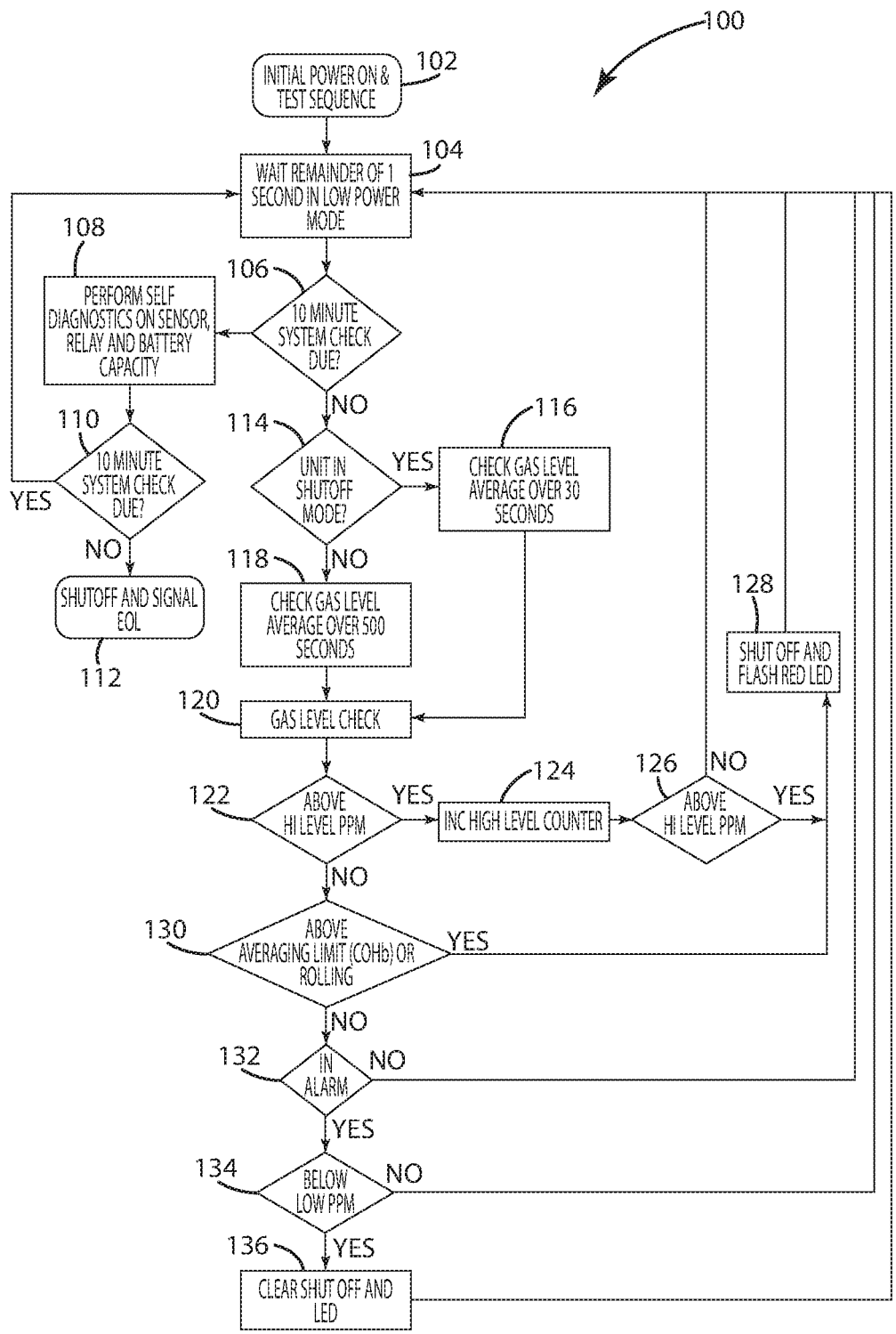
FIG. 3 is a flow chart of the control method of the present invention.

An exemplary method operation of the present invention may be best illustrated in flowchart in FIG. 3. As stated, it is expected that the system will be powered on at all times, so step 102 of initial power on and test sequence only needs to occur one time. Of course, as discussed above, for replaceable battery detectors or device powered systems 10, the initial step 102 may occur more than once. The initial step 102 of initial power on and test may occur at the factor, including during testing of the accuracy of the detector, or for example, the user may remove a pull tab that interrupts the battery connectivity upon set up of the device.

The system 20 may have a low power mode, as illustrated by the wait in low power mode step 104 in FIG. 3, of the overall method 100. Generally speaking, the low power mode is not required, but helpful in extending battery life. As illustrated, the "wait step" before starting the method is really the start, as numerous steps come back to this step 104 to start the method 100 over again. The system check step time 106 is illustrated as occurring every 10 minutes, but the time may vary. The system check step time 106 does not provide a timed interval to check for carbon monoxide levels, but instead when a positive answer to the system check step time is answered, the system self diagnostic step 108 is performed, which monitors battery capacity and status of the control actuator 50, such as a relay, and sensor 40 status. If all the systems pass during the system test, the system starts again at the beginning step 104. If it does not pass the self-diagnostic step, then the system test pass/fail step 110 provides an end of life or failure signal status step 112.

If the system determines in the time step 106 that it is not time for a system check, the unit makes a determination if the unit is in shutoff mode 114. If it is in Shutoff mode (control actuator 50 is in a position to ensure the device 10 is in an off state), the shutoff determination step 114 has the system 20 review the gas level over a time average of 30 seconds 116, instead of the 600 seconds 118 average if the device has not already been shut off or is in an off state with the control actuator 50. The step of sensing the carbon monoxide level, or a gas level check step 120 follows.

After sensing the carbon monoxide level 120, the controller 30 determines if the level of carbon monoxide sensed exceeds a predetermined level 122. If the answer is yes, the controller counts 124 the number of times the system exceeds the maximum predetermined level 122. The controller 30 then determines if the number of times exceed three readings above the predetermined level 126. If it does not exceed three times, the controller proceeds to step 104 as illustrated in FIG. 3, or in some instances right back to sensing carbon monoxide step 120. If the counter does exceed three (or any predetermined number) in the counting comparison step 126, the system will initiate the step of changing the on state to the off state with the control actuator, such as in the activating of the control actuator with the controller step 128.

If the controller determines that the level of carbon monoxide sensed does not exceed a preset maximum threshold 122, the controller determines if there is a rising average of carbon monoxide levels 130. If there is a rising level of carbon monoxide sensed, the controller proceeds to the activating the control actuator step 128 to shut off the device 10. Of course, the maximum and rising average steps could be switched in order, or done simultaneously. If there is no rising average, the controller looks to see if the system is currently in the shutoff state or in a control state to prevent the device from running or operating 132. If the controller 30 determines that no alarm exists, i.e. shutoff condition, it proceeds back to the beginning in step 104 or 120. If an alarm or shutoff condition is existing when the controller determines that there is no rising average or no maximum level exceeded, the controller may require the carbon monoxide level to fall below a minimum threshold before allowing the control actuator 50 to reset to a "run" or "on" state for the device 10, and the controller uses the readings from the sensor to determine that the minimum threshold is met 134. It should be noted that a counter step, such as step 124, may be added to ensure that the system reads the carbon monoxide is below the minimum threshold for a certain number of cycles or some time limit. If all of these conditions are met, the system may engage the control actuator to allow the device to run 136, and as part of this step clear any LED notifications.

Obviously, many modifications and variations of the present invention are possible in light of the above teachings and may be practiced otherwise than as specifically described while within the scope of the appended claims.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. Those skilled in the art will recognize that concepts disclosed in association with an example switching system can likewise be implemented into many other systems to control one or more operations and/or functions.

What is claimed is:

1. A method of controlling a device having an on-state and an off-state and capable of producing carbon monoxide in the on state, the control system including a control actuator, a sensor, and a controller in communication with the control actuator and the sensor, said method comprising:

sensing with the sensor a carbon monoxide level proximate to the device;

communicating the carbon monoxide levels from said step of sensing to the controller;

determining with the controller based on communicated carbon monoxide levels if the device is located in an enclosed area or outdoors;

activating the control actuator with the controller to ensure that the device is in the off-state in response to determining that the device is located in an enclosed are during said step of determining.

2. The method of claim 1 further including the steps of:

determining that the carbon monoxide level does not exceed a predetermined threshold; and determining that the carbon monoxide level does not exceed a predetermined rising average.

3. The method of claim 2 further including the steps of:

determining that the carbon monoxide levels are below a preset low threshold;

deactivating the control actuator to allow the control actuator to enter a run state in response to determining that the carbon monoxide levels are below a preset low threshold; and clearing any alarm conditions.

4. The method of claim 3 further including repeating the cycle of steps at regular intervals.

5. A method of controlling a device having an on-state and an off-state and capable of producing carbon monoxide in the on state, the control system including a control actuator, a sensor, and a controller in communication with the control actuator and the sensor, said method comprising:

sensing with the sensor a carbon monoxide level proximate to the device;

communicating the carbon monoxide levels from said step of sensing to the controller;

determining with the controller the presence of a rising average of carbon monoxide levels and determining if the device is located in an enclosed space or outside and activating the control actuator with the controller to ensure that the device is in the off-state in response to determining that the device is located in an enclosed space;

comparing the rising average of carbon monoxide levels to a predetermined rising average threshold level, upon determining that a rising average of carbon monoxide levels exists during said determining step;

activating the control actuator with the controller to ensure that the device is in the off-state in response to said step of comparing showing that the rising average of carbon monoxide levels exceeds the predetermined threshold.

6. The method of claim 5, wherein said step of determining includes the step of determining a rising average over a set period of time.

7. The method of claim 5 wherein said steps of sensing, determining, comparing and activating occur before a user attempts to initiate the on state with the device.

8. The method of claim 7 further including a step of preventing initiation of the on state with the control actuator in response to the rising level of carbon monoxide exceeding the predetermined threshold level in said step of comparing.

9. The method of claim 8 wherein said step of determining also includes determining with the controller if the level of carbon monoxide sensed in said step of sensing exceeds a predetermined level.

10. The method of claim 7 further including a step of changing the on state to the off state with the control actuator in response to determining that the level of carbon monoxide exceeds a rising average, in said step of determining.

11. The method of claim 7 further including a step of preventing initiation of the on state with the control actuator in response to determining that the level of carbon monoxide exceeds a maximum threshold.

12. The method of claim 7 further including a step of changing the on state to the off state with the control actuator in response to determining that the level of carbon monoxide exceeds a maximum threshold.

13. The method of claim 5 wherein said step of sensing includes measuring the current output of the sensor and further including the step of calculating the accumulation levels of carboxyhemoglobin that would be occurring in the human body.

14. The method of claim 5 further including a step of performing a self-diagnostic on at least one of the carbon monoxide sensor, control actuator and battery capacity.

15. The method of claim 5 further including a step of determining the carbon monoxide levels are below a preset low limit while said control actuator is in the off-state in response to said step of activating and further including the step of instructing the control actuator with the controller to be in the on-state.

16. The method of claim 15 further including the step of clearing alarm indicators in response to said step of determining the carbon monoxide levels are below a preset low limit.

17. The method of claim 15 further include a step of multiple cycles of determining the carbon monoxide levels are below a preset low limit before performing said step of instructing the control actuator with the controller to be in the on-state.

\* \* \* \* \*